United States Patent [19]

Thomsen

[11] Patent Number: 4,908,018
[45] Date of Patent: Mar. 13, 1990

[54] METHOD AND APPARATUS FOR INJECTING FLUIDS INTO AN IV LINE

[76] Inventor: John Thomsen, 1749 Bay Shore Rd., Nokomis, Fla. 34275

[21] Appl. No.: 251,466

[22] Filed: Sep. 29, 1988

Related U.S. Application Data

[63] Continuation-in-part of Ser. No. 66,083, Jun. 24, 1987, abandoned.

[51] Int. Cl.⁴ .................................................. A61M 37/00
[52] U.S. Cl. ........................................ 604/83; 137/903; 604/247
[58] Field of Search .................. 604/83, 247; 137/903

[56] References Cited

U.S. PATENT DOCUMENTS

| 3,399,677 | 9/1968 | Gould et al. | 137/903 X |
| 3,994,293 | 11/1976 | Ferro | 604/83 |
| 4,597,511 | 7/1986 | Licari | 137/903 X |
| 4,666,429 | 5/1987 | Stone | 604/83 |

Primary Examiner—Allen M. Ostrager
Attorney, Agent, or Firm—Dominik, Stein, Saccocio, Reese, Colitz & Van Der Wall

[57] ABSTRACT

Apparatus including a manifold and improved check valves for selectively injecting supplemental fluids into a closed IV line extending from a source of saline solution to a patient during an operation. Also disclosed are a plurality of connected manifolds and a device to secure the apparatus in location for easy administration of the supplemental fluids to the IV line.

5 Claims, 3 Drawing Sheets

METHOD AND APPARATUS FOR INJECTING FLUIDS INTO AN IV LINE

CROSS REFERENCE TO RELATED APPLICATION

This application is A Continuation-In-Part Application of co-pending U.S. patent application Ser. No. 07/066,083 filed June 24, 1987 in my name, now abandoned.

BACKGROUND OF THE INVENTION

1. Field of the Invention

This invention relates to the injection of supplemental fluids, through an improved check valve, into an IV line and, more particularly, to a method and apparatus for selectively injecting supplemental fluids, through an improved check valve, into a closed intravenous channel which extends from a source of saline solution to a patient during an operation.

2. Description of the Background Art

For many years it had been a common practice to establish an intravenous (IV) line or channel from a supply of solution to a patient who is being operated upon. The line is generally established by tubing coupled at its upper end to a bottle of solution such as normal saline solution and at its lower end to the vein of a patient through a needle. Such an arrangement establishes a continuous, sterile, closed channel or line which allows for the quick introduction of supplemental fluids which might be needed during the operation. Supplemental fluids may be added to the solution in the tubing and thus provided to the patient through a manifold and valve arrangement located intermediate the ends of the tubing.

The large number of known devices and the extensive patent literature are evidence of the dissatisfaction which many medical people have with known intravenous systems and attest to their efforts to devise an optimum system. For example, supplemental fluids for IV lines are normally maintained in syringes couplable to the tubing and solution through selectively rotatable stopcocks. A conventional stopcock would allow for the passage of the channel fluid from its source of supply, its syringe, to the patient. Rotating the stopcock would shut off the supply of channel fluid and allow for the injection of the supplemental fluid through the tubing to the patient independent of the channel fluid. After injection of an appropriate quantity of supplemental fluid, the stopcock would be repositioned to preclude passage of additional supplemental fluid and to allow the continued flow of the solution. Under certain circumstances, if the stopcock of the prior art were not promptly returned to its position to preclude the flow of supplemental fluid, there could be a reverse flow to allow entry of solution into the syringe to contaminate the supplementary fluid.

Some forms of stopcocks are configured to allow for the passage of solution but include two ports, one associated with each side of the tubing. In the first position, the solution would flow directly to the patient with the injection of supplemental fluid being precluded. In second and third positions, the flow of solution would be stopped to allow introduction of either one supplemental fluid through a first supplemental port or the introduction of a second supplemental fluid from a second supplemental port. As in the first technique discussed above, the flow of fluids to the patient is from either the source of solution, the source of the first supplemental fluid, or the source of the second supplemental fluid, but never from any two sources simultaneously. Further, unnecessary attention must be paid to the position of the stopcock mechanisms to insure that the intended valve port to the intended syringe is being opened rather than the other.

In addition, other types of valves for adding supplemental fluid to a line can be found in the catheter art. Consider, for example, U.S. Pat. No. 3,192,949 to DeSee and 3,385,301 to Harautuneian. Additionally, U.S. Pat. Nos. 3,831,629 to Mackal et al; 4,209,485 to Greenspan; 4,429,856 to Jackson and 4,449,693 to Gereg disclose valves generally of the poppet type for uses in other than providing supplemental fluids to IV lines, as for example, to catheters. The opening of the valve would be effected by contact from a hypodermic needle in the prior art or pressure from the fluid therefrom. The use of such valves, however, is not suggested in the prior art for other than their intended purposes and certainly not for use as a replacement for the stopcocks commonly used in association with IV lines.

An optimum system would be something new which combines the benefits of the prior practices without their shortcomings, i.e., something which provided for a large number of supplemental fluid ports for an IV line, the number being determined by an anesthesiologist for a particular operation and having the ability to allow for the injection of supplemental fluids into the flow of solution without closing off the primary flow of solution and without the possibility backflow of solution or other fluids into a syringe injecting the supplemental fluid.

As illustrated by the great number of prior patents as well as commercial devices, efforts are continuously being made in an attempt to inject supplemental fluids into IV channels more efficiently, conveniently, reliably and economically. None of these previous efforts, however, provides the benefits attendant with the present invention. Additionally, prior methods and apparatus do not suggest the present inventive combination of method steps and component elements arranged and configured as disclosed and claimed herein. The present invention achieves its intended purposes, objectives and advantages over the prior art devices through a new, useful and unobvious combination of method steps and component elements, with the use of a minimum number of functioning parts, at a negligible cost to manufacture, and by employing only readily available materials.

Therefore, it is an object of this invention to provide a method and apparatus for selectively injecting, through check valves, supplemental fluids into a closed intravenous line in tubing which extends from a source of saline solution to a patient during an operation.

A further object of the present invention is to increase the efficiency of check valves.

It is further object of the invention to preclude the backflow of fluids from an intravenous line into a syringe for injecting supplemental fluids into the intravenous line.

It is yet a further object of the invention to conveniently position any number of syringes with supplemental fluids into operative position with respect to an IV line.

Lastly, it is an object of the invention to inject any number of supplemental fluids, sequentially or concurrently, into the flow of solution in tubing to a patient being operated upon.

The foregoing has outlined some of the more pertinent objects of the invention. These objects should be construed to be merely illustrative of some of the more prominent features and applications of the intended invention. Many other beneficial results can be attained by applying the disclosed invention in a different manner or modifying the invention within the scope of the disclosure. Accordingly, other objects and a fuller understanding of the invention may be had by referring to the summary of the invention and the detailed description of the preferred embodiment in addition to the scope of the invention defined by the claims taken in conjunction with the accompanying drawings.

SUMMARY OF THE INVENTION

The invention is defined by the appended claims with a specific embodiment shown in the attached drawings. For the purpose of summarizing the invention, the invention may be incorporated into an assembly for use in creating a flow of solution through tubing to establish an IV line from a supply of solution to a patient during an operation and for allowing the selectively injecting of supplemental fluid under pressure into the flow of solution. The assembly comprises a manifold including a connector having a female taper at one end and a male taper at the other end releasably couplable with a length of tubing intermediate its length and having a cylindrical bore extending therethrough. The manifold also includes a plurality of risers extending radially from the connector with each riser having a bore extending therethrough in fluid communication with the bore of the connector. The assembly also comprises a check valve operatively associated with each riser. Each check valve includes a body positioned over the radially exterior end of a riser and has a cylindrical bore extending therethrough in fluid communication with the bore of its associated riser and the connector. The radially exterior end of each body is formed with a female taper for the support of a syringe adapted to provide a supply of supplemental fluid under pressure. Each check valve also includes a poppet positioned between its associated body and riser to seal the bore of the body for precluding the flow of supplemental fluids therethrough and, upon the application of the pressure of supplemental fluid from a syringe, to resiliently displace the poppet, to unseal the bore of the body and to thereby allow the flow of supplemental fluid from the syringe to the solution flowing through the connector and to the patient. Each body has a restricted central portion and each poppet has an imperforate upper portion positionable in sealing contact with the central portion of the body for precluding the flow of supplemental fluid from the syringe therethrough. Each poppet has resilient legs secured to the imperforate upper portion and positionable in contact with its associated riser to resiliently urge the imperforate upper portion into fluid sealing contact with the restricted central portion of the body, to allow the displacement of the imperforate upper portion with respect to the restricted central portion for the flow of supplemental fluid therethrough when pressurized, and to return the imperforate upper portion into fluid sealing contact with the restricted central portion of the body upon the relief of pressure from the supplemental fluid. The upper extent of each body portion is of a female frustroconical configuration.

In addition, for the purpose of summarizing the invention, the invention may be incorporated into a system for establishing a flow of solution to constitute a channel from a supply of solution to a patient during an operation and for selectively injecting supplemental fluid into the flow of solution. The system comprises a supply of solution positioned at a location elevated with respect to the patient receiving such solution and flexible tubing coupled at its upper end to the supply of solution and at its lower end to the patient thereby constituting a channel of solution therebetween. The system also includes manifold means operatively coupled with the tubing. The manifold means includes connector means with a cylindrical bore extending therethrough and has a female taper at one end and a male taper at the other end releasably coupled with the tubing at a location intermediate its ends. The manifold means also includes riser means extending radially from the connector means with a cylindrical bore extending therethrough in fluid communication with the bore of the connector means. The system also includes valve means operatively coupled with the manifold means. The valve means includes body means positioned over the end of the riser means remote from the connector means with a cylindrical bore extending therethrough in fluid communication with the bore of the riser means and the connector means. The valve means also includes poppet means positioned between the body means and the riser means to seal the bore of the body means for precluding the flow of supplemental fluids therethrough and, upon the application of the pressure from supplemental fluid, to resiliently displace the poppet means for opening the valve means and thereby allow the flow of supplemental fluid from exterior of the valve means to the flow of solution and the patient.

The system further includes syringe means removably coupled with the body means on the side thereof remote from the riser means for the retention of supplemental fluid and for the injection of such fluid into the solution through pressure sufficient to displace the poppet means and thereby allow its passage through the valve assembly. The manifold means may include a single connector means and a plurality of riser means coupled therewith and a plurality of body means and riser means equal in number to the riser means. The manifold means may include a plurality of connector means releasably connected with each other and coupled with the tubing. The female taper and the male taper of the connector means are of compatible sizes so that the female taper at one end of a manifold means may couple with the male taper of an associated manifold means. The system may include a plurality of manifold means coupled with respect to each other and to the tubing. The system further includes support means for the manifold means, the support means including a horizontal platform for retaining the manifold means in a predetermined orientation. The support means includes a vertical portion upstanding from the horizontal portion with C-shaped clips extending therefrom to support the syringe means in a fixed, essentially upright orientation. The system further includes hook means coupled to the upper extent of the vertical portion for retaining the support means on a fixed surface in a predetermined orientation.

The invention may also be incorporated into an assembly for use in creating a flow of solution through tubing to establish an IV line from a supply of solution to a patient during an operation and for allowing the selectively injecting of supplemental fluid under pressure into the flow of solution. The assembly comprises a manifold including a connector having a first end and a second end couplable with a length of tubing intermediate its length and having a cylindrical bore extending therethrough, the manifold also including riser means extending radially from the connector with each riser means having a bore extending therethrough in fluid communication with the bore of the connector; and a check valve operatively associated with the riser means with each check valve including a body positioned adjacent to the radially exterior end of the riser means and having a cylindrical bore extending therethrough in fluid communication with the bore of its associated riser means and the connector, each body being formed for the support of a syringe in order to facilitate the flow of supplemental fluid under pressure, each check valve also including a poppet positioned between its associated body and riser means to seal the bore of the body for precluding the flow of supplemental fluids therethrough and, upon the application of the pressure of supplemental fluid from a syringe, to resiliently displace the poppet, to unseal the bore of the body and to thereby allow the flow of supplemental fluid from the syringe to the solution flowing through the connector and to the patient.

The invention may also be incorporated into an improved check valve for use in effecting the flow of fluid from one location to another. The check valve comprises a poppet having an upper imperforate cap and lower depending legs, the legs being formed as a discontinuous cylinder for buckling under the application of pressure from fluid to be passed therethrough, the legs including slots and apertures with axial and radial portions. The apertures extend axially along the majority of their lengths and then horizontally adjacent to the cap. The check valve further includes a riser having a surface for receiving the legs, the riser including retaining lips with their radially exterior surfaces adapted to receive the radial interior surfaces of the legs. The check valve upper edges of the retaining lips are chamfered in a first direction and the lower edges of the legs are chamfered in a mating directing to facilitate the mating thereof during assembly.

The invention may also be incorporated into an assembly for use in creating a flow of solution through tubing to establish an IV line from a supply of solution to a patient during an operation and for allowing the selectively injecting of supplemental fluid under pressure into the flow of solution. The assembly comprises a manifold including a connector having a first end and a second end couplable with a length of tubing intermediate its length and having a cylindrical bore extending therethrough, the manifold also including riser means extending radially from the connector with each riser means having a bore extending therethrough in fluid communication with the bore of the connector; and a check valve operatively associated with the riser means with each check valve including a body positioned adjacent to the radially exterior end of the riser means and having a cylindrical bore extending therethrough in fluid communication with the bore of its associated riser means and the connector, each body being formed for the support of a syringe in order to facilitate the flow of supplemental fluid under pressure, each check valve also including a poppet positioned between its associated body and riser means to seal the bore of the body for precluding the flow of supplemental fluids therethrough and, upon the application of the pressure of supplemental fluid from a syringe, to resiliently displace the poppet, to unseal the bore of the body and to thereby allow the flow of supplemental fluid from the syringe to the solution flowing through the connector and to the patient, each poppet having an upper imperforate cap and lower depending legs, the legs being formed as a discontinuous cylinder for buckling under the application of pressure from fluid to be passed therethrough, the legs including slots and apertures with axial and radial portions.

Lastly, for the purposes of summarizing the invention, the invention may be incorporated into a method of generating an IV line in tubing through the flow of solution from a source of supply to a patient during an operation and for selectively injecting supplemental fluid into the flow of solution. The method comprises (1) positioning a supply of solution at a location elevated with respect to the patient receiving such solution; (2) providing flexible tubing coupled at its upper end to the supply of solution and at its lower end to the patient for establishing a line of flowing solution therebetween; (3) positioning a manifold at an intermediate point along the length of the tubing the manifold including a connector having a female taper at one end and a male taper at the other end and having a cylindrical bore extending therethrough releasably coupled to the tubing intermediate its ends, the manifold also including risers extending radially from the connector with each riser having a bore extending therethrough in fluid communication with the bore of the connector; (4) providing a valve operatively coupled with each riser, each valve including a body positioned over the end of each riser remote from the connector with a cylindrical bore extending therethrough in fluid communication with the bore of its associated riser, each valve also including a poppet positioned between each body and riser to seal the bore of the body for precluding the flow of supplemental fluid therebeyond and, upon the application of the pressure of supplemental fluid, to resiliently displace the poppet, to open the valve and thereby allow the flow of supplemental fluid from exterior of the valve to the flow of solution in the connector; (5) resiliently urging an imperforate upper portion of each poppet in contact with a restricted central portion of its associated body to effect a fluid sealing contact; (6) selectively applying pressure to the upper portion of a selected poppet through supplemental fluid to displace the poppet and allow the separation thereof from its associated body at its restricted central portion for the flow of supplemental fluid therethrough to the flow of solution in the connector and to the patient; and (7) selectively relieving the pressure of the supplemental fluid to resiliently return the imperforate upper portion of the displaced body into fluid sealing contact with the restricted central portion of the body means upon the relief of pressure by the supplemental fluid.

The method further includes the step of positioning a platform in an essentially horizontal orientation adjacent to the manifold and positioning the manifold on the platform. The method further includes the step of providing a plurality of resilient C-shaped clips on an upwardly extending vertical portion of the platform and supporting, in each C-shaped clip, a syringe operatively coupled to the radially exterior end of each body. The method further includes the step of providing a plurality of manifolds connected end to end at the intermediate point along the length of the tubing.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other methods and structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be had to the following detailed description taken in connection with the accompanying drawings in which.

Similar reference characters refer to similar parts through the several views of the drawings.

DETAILED DESCRIPTION OF THE INVENTION

Figure 1:
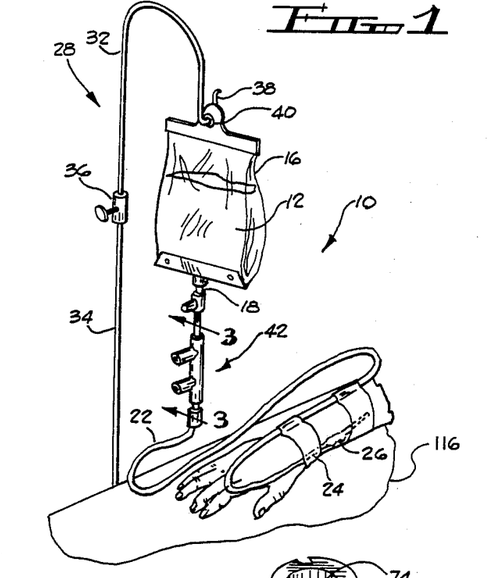
FIG. 1 is an isometric view of an intravenous system constructed in accordance with the principles of the present invention, the system being operatively coupled with a patient.

Shown in FIG. 1 is a system 10 for introducing intravenous or IV channel solution 12 to a patient during an operation with the system having the capability of allowing for the selective introduction of supplemental fluid 14 into the solution at the discretion of an anesthesiologist. The system includes a bag 16 of solution, such as normal saline, coupled to the upper end 18 of tubing 22 for conveying the solution therethrough. A valve such as a ball valve or a stopcock or the like may be provided along the length of the tubing 22 adjacent to the bag 16 to preclude the reverse flow of solution or other fluid from the tubing into the bag or to stop the flow of solution from the bag into the tubing. The lower end 24 of the tubing 22 includes a needle 26 inserted into the vein of the patient. The bag 16 is supported at an elevation above the patient to effect the gravity flow of the solution 12 to the patient. A stand 28 formed of telescopic segments 32 and 34 movable with respect to each other through a set screw 36 is adapted to support the bag 16 at an appropriate height for effecting appropriate pressure causing the fluid to flow to the patient. A hook 38 at the top of the support stand 28 supports and retains the bag 16 at the appropriate height through a hole 40.

The fluid channel solution being provided might be other than normal saline (0.9 NS). It might be Dextrose (D5W) or other channel solution or combinations thereof. The solution and its point of entry to the patient are functions of the nature of the operation to be performed as well as the nature and condition of the patient. The channel or line normally begins at bag 16 and ends with a needle coupled to a patient's vein in an arm, although it might be coupled to a vein or artery in another body part, such as the neck.

The solution has for its main purpose the establishment of a channel or line for the quick introduction of supplemental fluids that might be needed during an operation. It may also simply replenish the natural fluids of the patient's body. Supplemental fluids 14 that might be added include, anesthetics, antibiotics, heart medication, anti-arrhythmics, blood, plasma and the like. Such supplemental fluids might be planned beforehand because of the nature of the operation and the patient. Alternatively, they might be made available as a function of things which might be necessitated in the event of a complication during the operation.

Some operations may be set up for the addition of but one or two supplemental fluids. Other operations, such as open heart surgery, might be set up for the introduction of four or five or more types of supplemental fluids. Such supplemental fluids are normally given sequentially but in some instances might be given simultaneously so long as such supplemental fluids are not mutually incompatible. Determination of the addition of such supplemental fluids, including their quantities, is generally done directly by the anesthesiologist standing with the solution 12 and supplemental fluids 14 adjacent to the head of the patient. The addition of the supplemental fluids may be done by another at the direction of the anesthesiologist.

Figures 5A, 5B, 6, 7, 8:
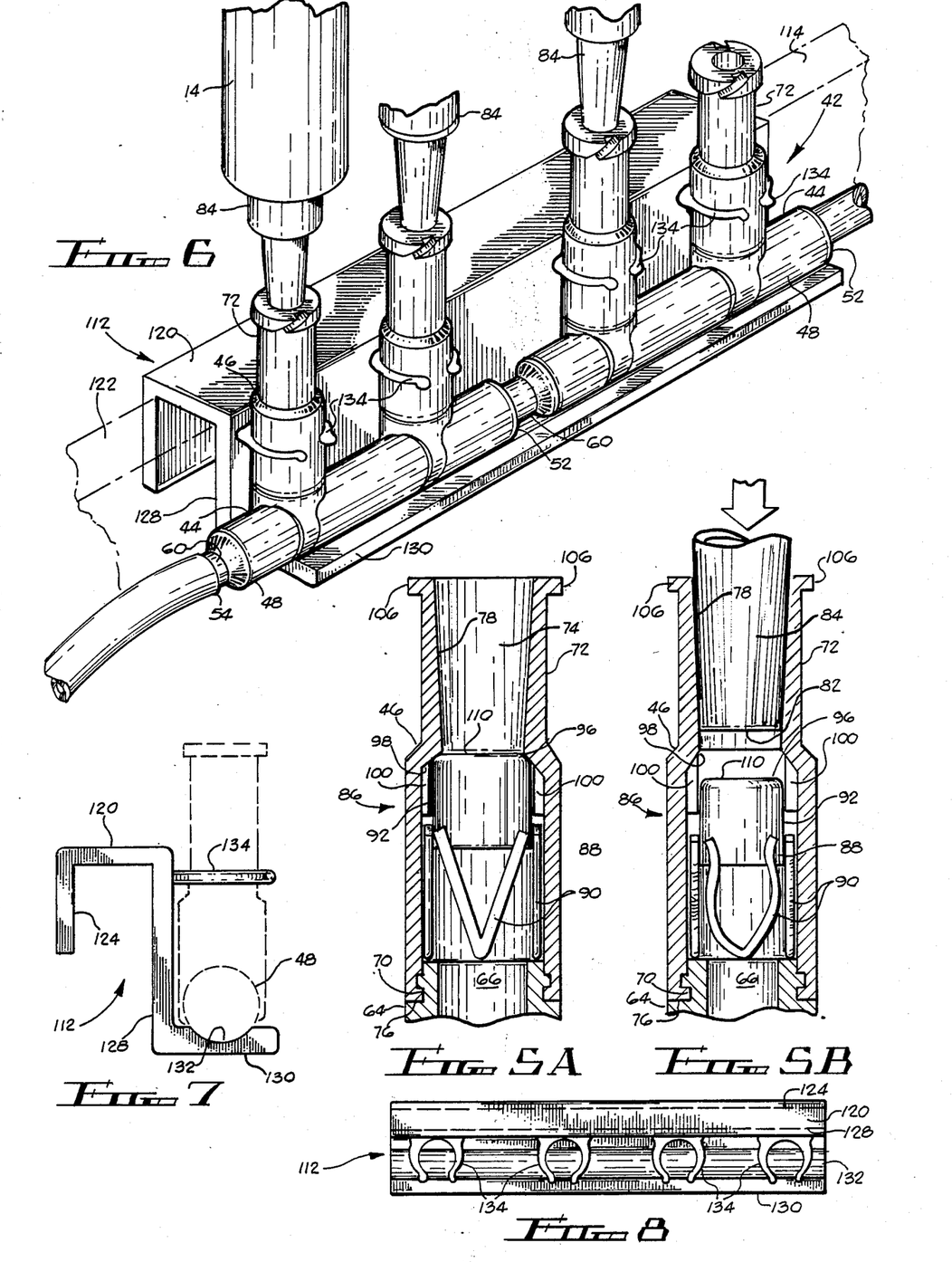
FIGS. 5A and 5B are sectional views taken along line 5—5 of FIG. 3 illustrating the valve in the closed and open positions respectively.
FIG. 6 is an enlarged isometric illustration of the apparatus shown in FIGS. 1 through 5 but illustrating two intravenous assemblies in operative association and located on a support member.
FIG. 7 is an end elevational view of the support member shown in FIG. 6.
FIG. 8 is a plan view of the support member shown in FIGS. 6 and 7.

Located intermediate the ends 18 and 24 of the tubing 20 is the intravenous assembly 42 including a manifold 44 or manifolds and their associated check valves 46. Each manifold 44 includes an essentially rigid plastic connector 48, having a bore 50 extending axially therethrough. The connector 48 is adapted to be coupled into the tubing 22 intermediate its ends as through the press fitting therebetween. The input end 52 and the output end 54 of the connector 48 are tapered for the appropriate male and female coupling to the intermediate portions of the tubing 22 as shown. The input end 52 includes a female tapered bore 58 which constitutes a Lure taper of about 6 percent as is conventional and standard in the industry. Its diameter at an intermediate axial extent is substantially the same as the exterior diameter of the tubing 22. The output end 54 includes a male tapered bore 60, again at a Lure angle of about 6 percent, and, at an intermediate axial extent has a diameter substantially equal to the interior diameter of the tubing 22. Because of the size and shape of the ends of the connector 48, the tubing may be press fit therewith so that the bore 50 of the connector 48 will constitute a continuation of the tubing 22 between the bag 16 and the patient. In the alternative, a plurality of intravenous assemblies 42 with their manifolds 44 may be interconnected as shown in FIG. 6 with their adjacent ends coupled to each other and their remote ends coupled to the tubing 22.

Figure 2:
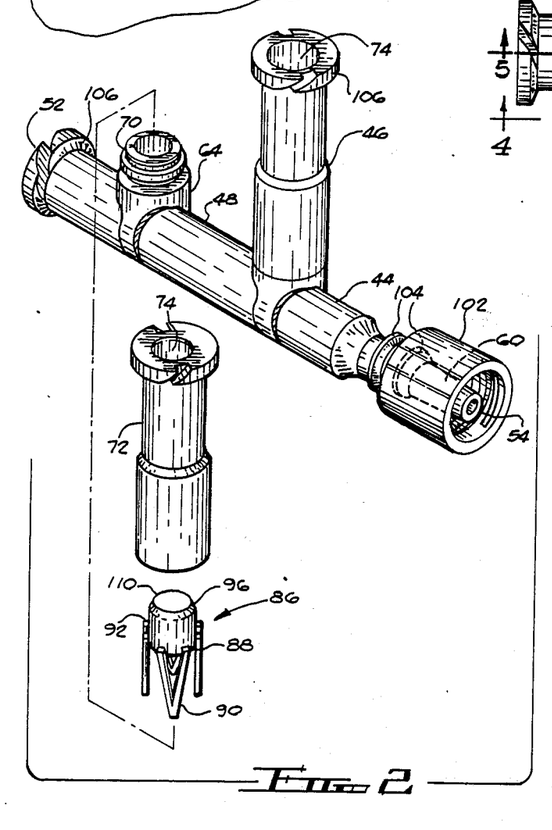
FIG. 2 is an enlarged exploded isometric view of the intravenous assembly for injecting supplemental fluids into the tubing for intermixing with the channel solution as shown in FIG. 1 but viewed horizontally rather than vertically.
Figure 3:
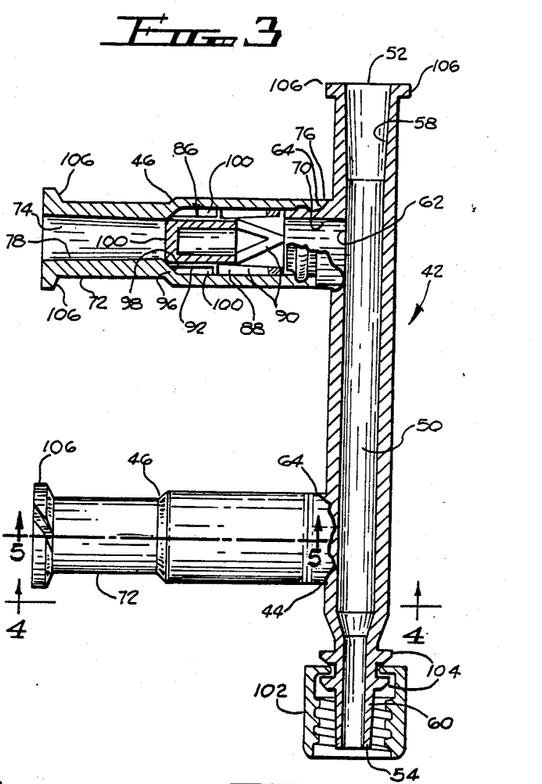
FIG. 3 is an enlarged view, partially in section, of the intravenous assembly including manifold and check valves with associated components as shown in FIGS. 1 and 2.
Figure 4:
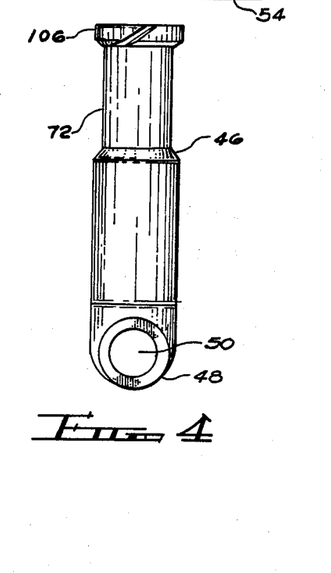
FIG. 4 is a sectional view of the assembly shown in FIG. 3 taken along line 4—4 of FIG. 3.

Formed in the surface of each connector 48 are a plurality of apertures 62 and associated cylindrical risers 64. Each riser is provided with a bore 66 which extends radially from the connector and is in open contact therewith so that supplemental fluids 14 may be introduced through the risers 64 to the bore 50 of the connector 48. The radially exterior end of each riser 64 is provided with a circumferentially reduced portion or recess 70 on its exterior surface for the receipt of a valve body 72.

The valve body is formed of an elastomeric material and is shaped in a generally cylindrical configuration with a central axial bore 74 of a diameter to be received, at its radial interior end, over the radial exterior end of the riser 64. A circumferential interior projection 76 on the valve body, coupled with the circumferential exterior recess 70 in the riser 64, effects their tight coupling and separation due to the resilience of the body. The upper interior portion of the body, radially exterior of the riser, has an internal female conical taper 78, again of 6 percent representing the conventional industry standard, for the receipt of the needleless end 82 of a syringe 84. Taper 78 is configured and sized so that an inserted syringe 84 extends therein to an intermediate point along the length of the taper.

The second part of the check valve 46 is a poppet 86 which is positioned within the body 72 adjacent to the riser 64. The poppet has an intermediate section 88 with resilient buckling legs 90 in V-shaped configurations extending downwardly therefrom in contact with the riser. The poppet also has an upwardly extending imperforate cap 92 of a cylindrical configuration with a curved shoulder constituting a bearing surface 96. The cap extends upwardly into a tapering intermediate portion 98 of the body 72 with its bearing surface 96 in intimate sealing contact with the tapering, conical intermediate portion 98 of the body 72. Ribs 100 are located within the valve body 72 adjacent to, and parallel with, the poppet 86 to insure that the movement of the poppet remains axial during its opening and closing. The bearing surface 96 of the cap 92 and the tapering intermediate portion 98 of the body 72 are of mating configurations whereby, when operatively positioned between the riser and body, the legs 90 of the poppet 86 will be supported on the upper surface 110 of the riser so that the cap 92 and the body 72 form a fluid tight seal therebetween.

Upon reaching a predetermined limit as determined by the strength of the legs, pressure applied to the upper surface of the cap 92 of the poppet 86 by the pressurized supplemental fluid from the syringe will cause the cap to move downwardly, further buckling the legs 90 of the poppet 86 and providing a path for fluid flow from above the body, past the poppet and into the bore of the tubing. Note FIG. 5B. Relieving the pressure will cause the legs to resile to their more extended sealing positions seating the bearing surface 96 of the cap against the conical intermediate surface of the body. Note FIG. 5A. When the check valve is open, the pressure of the supplemental fluid from the syringe which opened the poppet will cause the fluid to flow into the tubing and be carried with the channel fluid into the patient. In addition, the flow of solution through the connector will draw the supplemental fluid into the channel and also draw off any fluid within the riser or body even after the valve is resealed.

The ends of the connectors with their female and male Lure shapes are readily adapted for coupling with the tubing conveying the solution. The shapes of these ends, however, are also configured so as to allow the coupling of two or more valve assemblies together as a function of the patient and operation to be performed. As a result, the system can support any number of syringes, to dispense any number of supplemental fluids sequentially or concurrently, by simply coupling together any number of valve assemblies. Coupling of the ends of the valve assemblies may be made further secure by nuts 102, rotationally secured with respect to the male end of the manifold 44. Annular collars 104 receive the inboard ends of the nuts which are received between the collars to preclude their axial movement while allowing for their rotation. Internal threads within the nuts may thus be rotated to threadedly engage and disengage the threaded teeth 106 radially extending from the female end of the manifold. Threaded teeth 106 may also be provided on the ends of the valve bodies 72 for coupling with rotatable nuts, similar to those as described above, as are often provided on syringes.

The syringes are conventional in their design with a cylindrical central portion for retaining the supplemental fluid to be dispensed, with a plunger at its upper end under the control of an operator to apply pressure to the supplemental fluid in the cylinder and thereby dispense the contained fluid, and with an opening at its lower end through which the retained supplemental fluid may be dispensed.

In order to simplify the use of a larger number of assemblies and syringes, the system is provided with a support member 112 with a generally J-shaped cross-sectional configuration positionable adjacent to the head end 114 of the operating table 116 near the location where the anesthesiologist would stand during the administration of such supplemental fluids. The support device has a horizontally disposed intermediate section 120 positionable over an end part 122 of the operating table with a short vertical section 124 extending downwardly in an adjacent slot of the operating table. A longer vertically disposed section 128 extends downwardly from the other end of the horizontal intermediate section 120. Outwardly extending from the longer vertical section in a direction away from the intermediate section is a ledge 130 with a channel receiving recess 132 for supporting the valve assembly or assemblies. Also used in association therewith are resilient C-shaped clips 134 to retain the risers and covers in a generally vertical, upwardly directed orientation for ease of identification and use by the operator.

The support member 112 may be of any predetermined length with any predetermined number of clips 134. In this manner, the support member and clips may be formed as a single member for providing support for any number of syringes 84 along with the corresponding number of supplemental fluids 14 as may be required for a particular operation and patient. In this manner, the plurality of syringes and supplemental fluids may be conveniently located under the control of the anesthesiologist for greater efficiency of utilization.

When intravenous assemblies 42 are coupled together, their associated plurality of syringes 84 are oriented in a generally equally spaced parallel relationship defined by the positions of the ledge 130 and C-shaped clamps 134 all located for the convenient control of the anesthesiologist. The anesthesiologist may thus activate any one or plurality of syringes sequentially or concurrently in the conventional manner to effect the intended injection of supplemental fluids into the solution as required.

In operation and use, a supply of channel solution 12 is positioned at a location elevated with respect to the patient receiving such solution. Flexible tubing 22 is then provided to couple, at its upper end 18, to the supply of solution and, at its lower end 24, to the patient for establishing a channel or line of flowing solution therebetween. An intravenous assembly 42 is then positioned at an intermediate point along the length of the tubing 22. The intravenous assembly 42 includes a manifold 44 with a connector 48 having a female tapered bore 58 at one end and a male tapered bore 60 at the other end. It also has a cylindrical bore 50 extending therethrough releasably coupled to the tubing 22 intermediate its ends 18 and 24. The intravenous assembly 42 also includes risers 64 extending radially from the connector 48 with each riser having a bore 66 extending therethrough in fluid communication with the bore 50 of the connector 48. A check valve 46 is then operatively positioned on each riser 64. Each check valve 46 includes a body 72 positioned over the end of each riser 64 remote from the connector 48 with a cylindrical bore 74 extending therethrough in fluid communication with the bore 66 of its associated riser 64 and the connector 48. A poppet 86 is positioned between each body 72 and riser 64 to seal the bore of the body for precluding the flow of supplemental fluid 14 therebeyond and, upon the application of the pressure of supplemental fluid 14 from a syringe 84, to resiliently displace the poppet 86, to open the valve 46 and thereby allow the flow of supplemental fluid from exterior of the valve to the flow of channel solution in the connector. The imperforate cap 92 of the displaced poppet 86 is then resiliently urged in contact with its associated intermediate portion 98 to effect a fluid sealing contact at the restricted central portion of the body. Pressure is then applied to the upper portion of a selected poppet or poppets 86 through supplemental fluid to displace the poppet and allow the separation thereof from its associated valve body 72 at its restricted central portion for the flow of supplemental fluid therethrough to the flow of channel solution in the connector 48 and to the patient. Pressure of the supplemental fluid is then relieved to resiliently return the imperforate upper portion of the displaced poppet 86 into fluid sealing contact with the restricted intermediate portion 98 of the valve body 72 upon the relief of pressure by the supplemental fluid.

Figure 9:
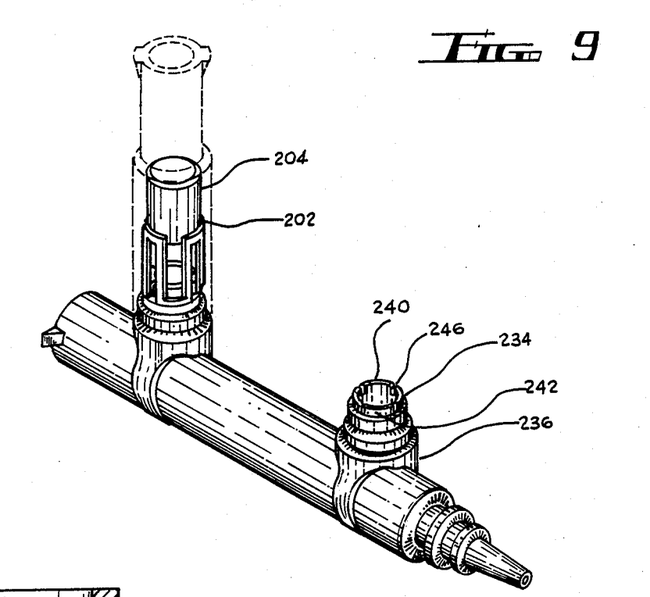
FIG. 9 is an enlarged isometric illustration of apparatus constructed in accordance with an alternate embodiment of the present invention.
Figure 10:
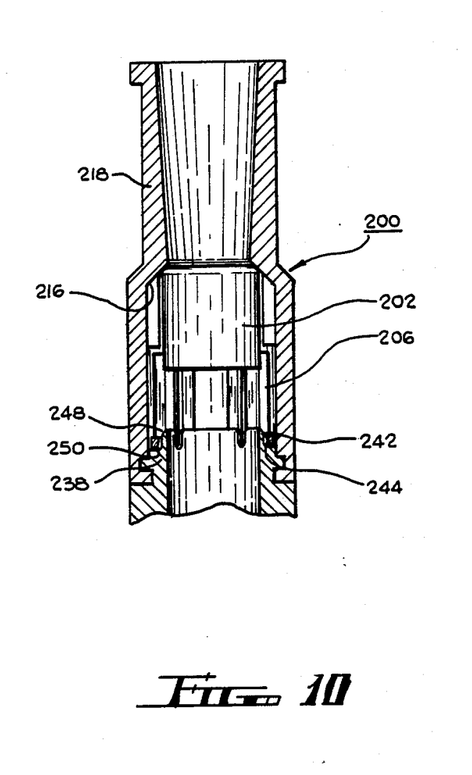
FIG. 10 is a sectional view taken radially through the check valve of FIG. 9.
Figure 11:
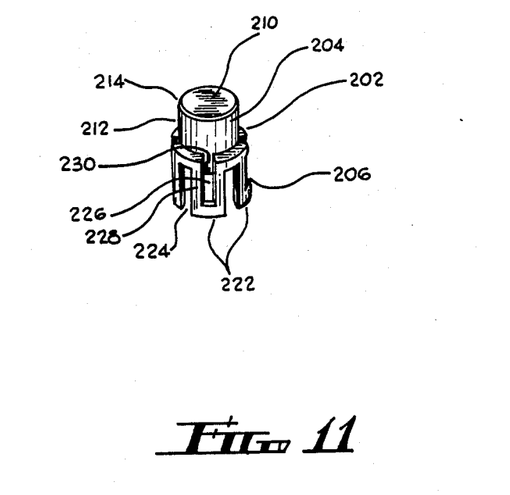
FIG. 11 is an isometric illustration of the poppet of the check valve shown in FIGS. 9 and 10.

Shown in FIGS. 9, 10 and 11 is an improved check valve 200, an alternate embodiment of the present invention which may be used with the apparatus shown in the embodiment of FIGS. 1-8. The improved check valve 200, like that of the primary embodiment, is formed of poppet 202 having an imperforate cap 204 at its upper extent and having depending buckling legs 206 at its lower extent. The entire poppet 202 is preferably formed of a one-piece molded elastomer, silicone rubber being the preferred material.

The cap is formed of an upper, planar surface 210 and circumferential side walls 212 depending therefrom. Intermediate the top surface 210 and side walls 212 are curved edges 214 adapted to be resiliently seated in bearing engagement against the sloping interior portion 216 of the body 218 to form a seal.

The legs 206 extend downwardly from the lower edge of the cap 204 and form a cylindrical support for the poppet. The legs 206 are formed of a plurality of arcuate members 222 with axial slots 224 therebetween so that together the legs form a discontinuous cylinder with the axial slots 224 extending over the minority of their circumferential extent. The slots 224 extend upwardly from the lower edges of the legs 206 to adjacent to the lower edge of the cap 204. The slots 224 function to preclude the stoppage of fluid through the valve 200 when the cap 204 is fully depressed under the application of the pressure from the syringe. Rectangular apertures 226 are also formed in the legs 206 for further improvement of the flow of fluid. The apertures 226 are formed with vertical, axial openings 228 along the majority of their lengths but include horizontal, radial openings 230 at their upper extents. The flow of fluid through the valve 200 is thus between the vertical and horizontal openings 228 and 230 of the apertures 226 as well as through the slots 224.

The upper edge 234 of each riser 236 is adapted to receive the legs 206 of the poppet 202. The radially interior edge 238 of the upper edge 234 is provided with an upwardly extending retainer lip 240 adapted to receive, adjacent to its exterior surface 242, the interior surface 244 of the legs 206. Like the legs 206, the retaining lips form a cylinder. The cylinder is formed with axial slots 246 rendering the cylinder discontinuous to further facilitate fluid flow and also preclude the welling up of fluids between the retaining lip 240 and the radially interior surface of the body 218. The upper surface of each riser is planar at its radially exterior portion for the receipt and support of the legs 206.

The upper edge of the retaining lip is formed with a chamfer 248 extending downwardly from radially interior to exterior. The lower edge of the buckling legs 206 are formed with a chamfer 250 extending downwardly from interior to exterior. These mating chamfers 248 and 250 facilitate the assembly of the check valve 00 through the proper locating of the legs 206 of the poppet 202 into proper orientation with respect to the riser 236 and body 218.

In view of the improved constructions as described herein, the valve will function to more efficiently allow fluid flow from the syringe into the bore of the manifold when fluid pressure is applied, the poppet 202 receeds and the legs 206 resiliently buckle. The improved constructions also act to more positively shut off the flow of fluid to the bore of the manifold upon the cessation of fluid forces from the injecting fluid from the syringe. In this manner, black-flow of fluid to the hypodermic needle from the manifold and main channel is more positively precluded.

The present disclosure includes that contained in the appended claims as well as that of the foregoing description. Although this invention has been described in its preferred form with a certain degree of particularity, it is understood that the present disclosure of the preferred form has been made only by way of example and that numerous changes in the details of construction and combination and arrangement of parts may be resorted to without departing from the spirit of the invention.

Now that the invention has been described, what is claimed is:

1. An assembly for use in creating a flow of solution through tubing to establish an IV line from a supply of solution to a patient during an operation and for allowing the selective injecting of supplemental fluid under pressure into the flow of solution, the assembly comprising:

a manifold including a connector having a first end and a second end couplable with a length of tubing intermediate its length and having a cylindrical bore extending therethrough, the manifold also including riser means extending radially from the connector with each riser means having a bore extending therethrough in fluid communication with the bore of the connector; and a check valve operatively associated with the riser means with each check valve including a body positioned adjacent to the radially exterior end of the riser means and having a cylindrical bore extending therethrough in fluid communication with the bore of its associated riser means and the connector, each body being formed for the support of a syringe in order to facilitate the flow of supplemental fluid under pressure, each check valve also including a poppet positioned between its associated body and riser means to seal the bore of the body for precluding the flow of supplemental fluids therethrough and, upon the application of the pressure of supplemental fluid from a syringe, to resiliently displace the poppet, to unseal the bore of the body and to thereby allow the flow of supplemental fluid from the syringe to the solution flowing through the connector and to the patient, each poppet having an upper imperforate cap and lower depending legs, the legs being formed as a discontinuous cylinder for buckling under the application of pressure from fluid to be passed therethrough, the legs including slots and apertures with axial and radial portions 2. An assembly for use in creating a flow of solution through tubing to establish an IV line from a supply of solution to a patient and for allowing the selective injecting of supplemental fluid under pressure into the flow of solution, the assembly comprising:

a manifold including a connector having a first end and a second end and having a bore extending therethrough, the manifold also including a riser extending radially from the connector with a bore extending therethrough in fluid communication with the bore of the connector; and a check valve operatively associated with the riser with the check valve including a body positioned adjacent to the radially exterior end of the riser and having a cylindrical bore extending therethrough in fluid communication with the bores of the riser and the connector, the body being formed for the support of a syringe in order to facilitate the flow of supplemental fluid under pressure, the check valve also including a poppet positioned between the body and the riser to seal the bore of the body for precluding the flow of supplemental fluids therethrough and, upon the application of the pressure of supplemental fluid from a syringe, to resiliently displace the poppet, to unseal the bore of the body and to thereby allow the flow of supplemental fluid from the syringe to the solution flowing through the connector and to the patient, the poppet having an upper imperforate cap and lower depending legs, the legs being formed as a discontinuous cylinder for buckling under the application of pressure from fluid to be passed therethrough, the legs including apertures extending axially along the majority of their lengths and then radially adjacent to the cap.

3. The assembly as set forth in claim 2 and further including axial slots formed in the legs between the apertures.

4. The assembly as set forth in claim 3 wherein the riser has a surface for receiving the legs, the riser including retaining lips with their radially exterior surfaces adapted to receive the radial interior surfaces of the legs.

5. The assembly as set forth in claim 4 wherein the upper edges of the retaining lips are chamfered in a first direction and the lower edges of the legs are chamfered in a mating direction to facilitate the mating thereof during assembly.

* * * * *